(12) United States Patent
Nagai et al.

(10) Patent No.: US 8,575,383 B2
(45) Date of Patent: Nov. 5, 2013

(54) SILSESQUIOXANE COMPOUND HAVING POLYMERIZABLE FUNCTIONAL GROUP

(75) Inventors: Akinori Nagai, Hiratsuka (JP); Yoshiaki Chino, Hiratsuka (JP); Masami Kobata, Hiratsuka (JP); Osamu Isozaki, Hiratsuka (JP)

(73) Assignee: Kansai Paint Co., Ltd., Hyogo (JP)

( * ) Notice: Subject to any disclaimer, the term of this patent is extended or adjusted under 35 U.S.C. 154(b) by 0 days.

(21) Appl. No.: 13/122,789

(22) PCT Filed: Sep. 9, 2009

(86) PCT No.: PCT/JP2009/065734
§ 371 (c)(1),
(2), (4) Date: Apr. 6, 2011

(87) PCT Pub. No.: WO2010/044321
PCT Pub. Date: Apr. 22, 2010

(65) Prior Publication Data
US 2011/0196059 A1    Aug. 11, 2011

(30) Foreign Application Priority Data
Oct. 15, 2008   (JP) ................................. 2008-266305

(51) Int. Cl.
*C07F 7/10*        (2006.01)
*C08F 2/46*        (2006.01)

(52) U.S. Cl.
USPC .............................................. 556/420; 522/1

(58) Field of Classification Search
None
See application file for complete search history.

(56) References Cited

U.S. PATENT DOCUMENTS

| 4,861,908 A | * | 8/1989 | Satoh et al. .................... 556/420 |
| 5,233,006 A | * | 8/1993 | Wolter et al. .................... 528/32 |
| 5,378,735 A | * | 1/1995 | Hosokawa et al. ............. 522/79 |
| 5,532,398 A | * | 7/1996 | Wolter et al. ................. 556/420 |
| 6,106,606 A | * | 8/2000 | Gellermann et al. ......... 106/441 |
| 7,385,017 B2 | | 6/2008 | Saito et al. |
| 7,977,404 B2 | | 7/2011 | Wolter et al. |
| 2006/0052567 A1 | | 3/2006 | Saito et al. |

FOREIGN PATENT DOCUMENTS

| EP | 332400 A2 * | 9/1989 |
| JP | 1-98609 | 4/1989 |
| JP | 3-281616 | 12/1991 |
| JP | 4-28722 | 1/1992 |
| JP | 2002-167552 | 6/2002 |
| JP | 2002-363414 | 12/2002 |
| WO | 2004/085501 | 10/2004 |
| WO | 2006/111373 | 10/2006 |

OTHER PUBLICATIONS

Examination Report for the corresponding UK Patent Application No. 1106131.4, 2012.
International Search Report issued Nov. 17, 2009 in International (PCT) Application No. PCT/JP2009/065734.

* cited by examiner

*Primary Examiner* — Robert S Loewe
(74) *Attorney, Agent, or Firm* — Wenderoth, Lind & Ponack, L.L.P.

(57) ABSTRACT

To provide a composition comprising a silsesquioxane compound that is capable of producing a coating film with excellent heat resistance and scratch resistance, and that has excellent compatibility with general polymerizable unsaturated compounds as well as polymerizable unsaturated compounds with high polarity.

A silsesquioxane compound comprising organic groups each directly attached to a silicon atom of the compound, at least one of the organic groups being an organic group having one or more urethane bonds and one (meth)acryloyloxy group.

4 Claims, No Drawings

SILSESQUIOXANE COMPOUND HAVING POLYMERIZABLE FUNCTIONAL GROUP

This application is a U.S. national stage of International Application No. PCT/JP2009/065734 filed Sep. 9, 2009.

TECHNICAL FIELD

The present invention relates to a silsesquioxane compound having a polymerizable functional group.

BACKGROUND ART

Silsesquioxane is a general term for a series of network-like polysiloxanes with a ladder, cage, or three-dimensional network (random) structure. Unlike silica, which is a complete inorganic material represented by general formula $SiO_2$, silsesquioxane is soluble in general organic solvents; therefore, it is easy to handle, and processability and moldability during membrane formation etc. are excellent.

On the other hand, as an unsaturated compound having radical polymerization properties, polyfunctional acrylate, unsaturated polyester, etc., are widely investigated, and are industrially used. Various studies are conducted on such radical-polymerizable unsaturated compounds for the purpose of providing scratch resistance, stain resistance, etc., with their cured products. However, a composition obtained by mixing an organopolysiloxane compound, such as silsesquioxane, with a widely used radical-polymerizable unsaturated compound has disadvantages such that a uniform composition is hard to produce because of its poor compatibility, and that an organopolysiloxane compound is separated from the resulting cured product.

Patent Documents 1 to 5 disclose inventions relating to silsesquioxane having a radical-polymerizable functional group such as an acryloyloxy or methacryloyloxy group, and an ultraviolet curable composition containing the silsesquioxane. Such silsesquioxane-containing compositions have excellent heat resistance and scratch resistance; however, silsesquioxane has a problem such that its compatibility with other polymerizable unsaturated compounds, in particular, with polymerizable unsaturated compounds having high polarity is insufficient.

CITATION LIST

Patent Literatures
PTL 1: Japanese Unexamined Patent Publication No. H3-281616
PTL 2: Japanese Unexamined Patent Publication No. H4-28722
PTL 3: Japanese Unexamined Patent Publication No. 2002-167552
PTL 4: Japanese Unexamined Patent Publication No. 2002-363414
PTL 5: WO04/85501

SUMMARY OF INVENTION

Technical Problem

The present invention was made in light of the aforementioned circumstances.

An object of the present invention is to provide a silsesquioxane compound that is capable of producing a coating film with excellent heat resistance and scratch resistance, and that has excellent compatibility with general polymerizable unsaturated compounds as well as polymerizable unsaturated compounds with high polarity.

Solution to Problem

The present inventors conducted extensive research to solve the above problems; consequently, they found that the aforementioned problems can be solved by introducing as an organic group directly attached to a silicon atom, an organic group having one or more urethane bonds and one (meth)acryloyloxy group into a silsesquioxane compound. The present invention was thus accomplished.

Specifically, the present invention is as follows:

Item 1

A silsesquioxane compound comprising organic groups each directly attached to a silicon atom of the compound, at least one of the organic groups being an organic group having one or more urethane bonds and one (meth)acryloyloxy group.

Item 2

The silsesquioxane compound according to Item 1, wherein the organic group having one or more urethane bonds and one (meth)acryloyloxy group is an organic group represented by the formula (A) below:

[Chem. 1]

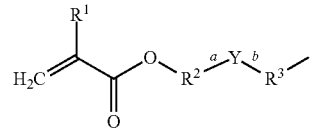

(A)

wherein $R^1$ represents a hydrogen atom or a methyl group, $R^2$ represents a $C_{1-10}$ divalent hydrocarbon group, $R^3$ represents a $C_{1-10}$ divalent hydrocarbon group, and Y represents

[Chem. 2]

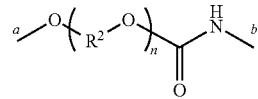

wherein $R^2$ is as defined above, and n represents an integer of 0 to 9;

[Chem. 3]

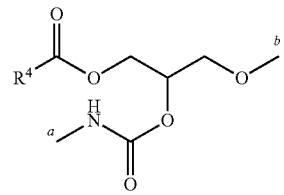

wherein R⁴ represents a substituted or unsubstituted $C_{1-6}$ monovalent hydrocarbon group; or

[Chem. 4]

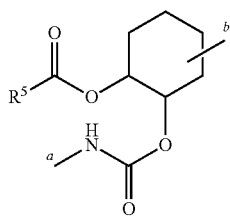

wherein R⁵ represents a substituted or unsubstituted $C_{1-6}$ monovalent hydrocarbon group.

Item 3

The silsesquioxane compound according to Item 1 or 2, wherein the weight average molecular weight is 1,000 to 100,000.

Item 4

An active energy ray-curable composition comprising the silsesquioxane compound according to any one of Items 1 to 3, and a photoinitiator.

Item 5

The active energy ray-curable composition according to Item 4, further comprising a polymerizable unsaturated compound.

Advantageous Effects of Invention

The silsesquioxane compound of the present invention can produce a silsesquioxane compound having excellent compatibility with general polymerizable unsaturated compounds as well as excellent compatibility with polymerizable unsaturated compounds having high polarity, by introducing as an organic group directly attached to a silicon atom, an organic group having one or more urethane bonds and one (meth)acryloyloxy group into the silsesquioxane compound.

Further, because of its excellent compatibility with various polymerizable unsaturated compounds, the silsesquioxane compound of the present invention can be used in various active energy ray-curable compositions, and can improve the heat resistance and scratch resistance of coating films that are obtained from the active energy ray-curable compositions.

DESCRIPTION OF EMBODIMENTS

The silsesquioxane compound of the present invention is a silsesquioxane compound comprising organic groups each directly attached to a silicon atom, wherein at least one of the organic groups is an organic group having one or more urethane bonds and one (meth)acryloyloxy group (hereinafter, sometimes simply referred to as "the silsesquioxane compound of the present invention").

Since at least one of the organic groups directly attached to a silicon atom in the silsesquioxane compound of the present invention is an organic group having one or more urethane bonds and one (meth)acryloyloxy group, the silsesquioxane compound has excellent compatibility with various polymerizable unsaturated compounds because of the polarity of the urethane bond(s) included in the organic group, and the silsesquioxane compound can be cured by active energy ray irradiation in the presence of a photoinitiator because of the (meth)acryloyloxy group included in the organic group.

For this reason, the silsesquioxane compound of the present invention is useable in various active energy ray-curable compositions.

Silsesquioxane Compound of the Present Invention

The silsesquioxane compound of the present invention has organic groups each directly attached to a silicon atom, in which at least one of the organic groups directly attached to a silicon atom is an organic group having one or more urethane bonds and one (meth)acryloyloxy group.

The term "silsesquioxane compound" used herein indicates not only a silsesquioxane compound having a structure in which all of the Si—OH groups (hydroxy silyl groups) are hydrolyzed and condensed, but also silsesquioxane compounds having a rudder structure, an incomplete cage structure, or a random structure, in which Si—OH groups remain.

In the silsesquioxane compound of the present invention, the proportion of the silsesquioxane compound having a structure in which all of the Si—OH groups are hydrolyzed and condensed is preferably 80 mass % or more, more preferably 90 mass % or more, and even more preferably 100 mass % or more in terms of liquid stability.

An example of the silsesquioxane compound of the present invention is a silsesquioxane compound in which an organic group having one or more urethane bonds and one (meth)acryloyloxy group is represented by the formula (A) below:

[Chem. 5]

(A)

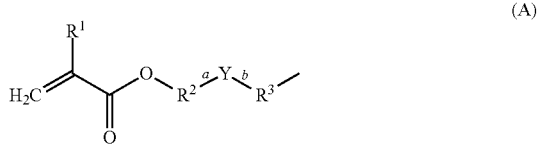

wherein R² represents a hydrogen atom or a methyl group, R² represents a $C_{1-10}$ divalent hydrocarbon group, R³ represents a $C_{1-10}$ divalent hydrocarbon group, and Y represents

[Chem. 6]

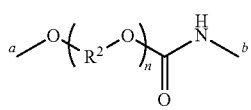

wherein R² is as defined above, and n represents an integer of 0 to 9,

[Chem. 7]

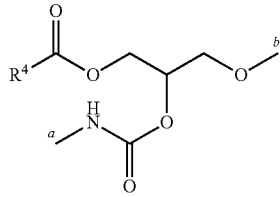

wherein R⁴ represents a substituted or unsubstituted $C_{1-6}$ monovalent hydrocarbon group, or

[Chem. 8]

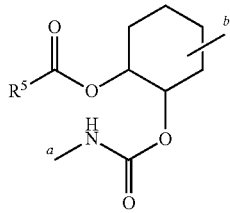

wherein R⁵ represents a substituted or unsubstituted $C_{1-6}$ monovalent hydrocarbon group.

The silsesquioxane compound of the present invention may include, among the organic groups represented by the formula (A) above, one kind of organic group, or two or more kinds of organic groups.

In other words, examples of the silsesquioxane compound of the present invention include a silsesquioxane compound in which an organic group having one or more urethane bonds and one (meth)acryloyloxy group is at least one member selected from the group consisting of organic groups represented by the formulae (I) to (III) below:

[Chem. 9]

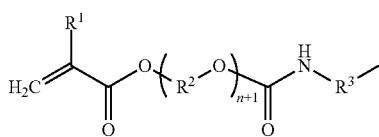

(I)

wherein R¹ represents a hydrogen atom or a methyl group, R² represents a $C_{1-10}$ divalent hydrocarbon group, R³ represents a $C_{1-10}$ divalent hydrocarbon group, and n represents an integer of 0 to 9;

[Chem. 10]

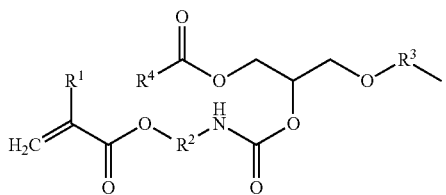

(II)

wherein R¹ to R³ are as defined above, and R⁴ represents a substituted or unsubstituted $C_{1-6}$ monovalent hydrocarbon group; or

[Chem. 11]

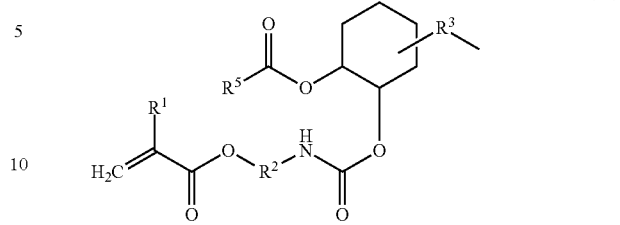

(III)

wherein R¹ to R³ are as defined above, and R⁵ represents a substituted or unsubstituted $C_{1-6}$ monovalent hydrocarbon group.

R² is not particular limited as long as it represents a $C_{1-10}$ divalent hydrocarbon group. Specific examples thereof include alkylene groups such as methylene, ethylene, 1,2-propylene, 1,3-propylene, 1,2-butylene, 1,4-butylene, and hexylene; cyclo alkylene groups such as cyclohexylene; arylene groups such as phenylene, xylylene, and biphenylene; and the like. Of these, $C_{1-6}$ divalent hydrocarbon groups, in particular, ethylene, 1,2-propylene, and 1,4-butylene are preferred because they have superior heat resistance, scratch resistance, and compatibility with polymerizable unsaturated compounds having high polarity.

R³ is not particularly limited as long as it represents a $C_{1-10}$ divalent hydrocarbon group. Specific examples thereof include alkylene groups such as methylene, ethylene, 1,2-propylene, 1,3-propylene, 1,2-butylene, 1,4-butylene, and hexylene; cyclo alkylene groups such as cyclohexylene; arylene groups such as phenylene, xylylene, and biphenylene; and the like. Of these, $C_{1-6}$ divalent hydrocarbon groups, in particular, ethylene and 1,3-propylene are preferred because they have superior heat resistance, scratch resistance, and compatibility with polymerizable unsaturated compounds having high polarity.

n is not particularly limited as long as it is an integer of 0 to 9. n is preferably an integer of 0 to 5, more preferably 0 to 3, and most preferably 0 or 1.

R⁴ is not particularly limited as long as it is a substituted or unsubstituted $C_{1-6}$ monovalent hydrocarbon group. Specific examples include monovalent acyclic aliphatic hydrocarbon groups or monovalent cyclic aliphatic hydrocarbon groups such as methyl, ethyl, n-propyl, isopropyl, n-butyl, isobutyl, tert-butyl, sec-butyl, n-pentyl, isopentyl, neopentyl, cyclopentyl, n-hexyl, isohexyl, cyclohexyl, and other straight or branched alkyl groups; trifluoromethyl, 3,3,3-trifluoro-n-propyl, and other fluorine-containing alkyl groups. Methyl is particularly preferred since it has excellent compatibility with a polymerizable unsaturated compound having high polarity.

R⁵ is not particularly limited as long as it is a substituted or unsubstituted $C_{1-6}$ monovalent hydrocarbon group. Specific examples include monovalent acyclic aliphatic hydrocarbon groups or monovalent cyclic aliphatic hydrocarbon groups such as methyl, ethyl, n-propyl, isopropyl, n-butyl, isobutyl, tert-butyl, sec-butyl, n-pentyl, isopentyl, neopentyl, cyclopentyl, n-hexyl, isohexyl, cyclohexyl, and other straight or branched alkyl groups; trifluoromethyl, 3,3,3-trifluoro-n-propyl, and other fluorine-containing alkyl groups. Methyl is particularly preferred since it has excellent compatibility with a polymerizable unsaturated compound having high polarity.

The organic group represented by the formula (I) is preferably an organic group in which R¹ is a hydrogen atom, R² is an ethylene group or a 1,4-butylene group, R³ is an ethylene group or a 1,3-propylene group, and n is 0 because it has superior heat resistance, scratch resistance, compatibility with a polymerizable unsaturated compound having high polarity, and active energy-ray curability.

The organic group represented by the formula (II) is preferably an organic group in which $R^4$ is a methyl group, $R^3$ is an ethylene group or a 1,3-propylene group, $R^1$ is a hydrogen atom, and $R^2$ is an ethylene group because it has superior heat resistance, scratch resistance, compatibility with polymerizable unsaturated compounds having high polarity and active energy-ray curability.

The organic group represented by the formula (III) is preferably an organic group in which $R^5$ is a methyl group, $R^3$ is an ethylene group or a 1,3-propylene group, $R^1$ is a hydrogen atom, and $R^2$ is an ethylene group because it has superior heat resistance, scratch resistance, compatibility with polymerizable unsaturated compounds having high polarity and active energy-ray curability.

The silsesquioxane compound of the present invention may have a single composition or a mixture of compounds having different compositions.

The weight average molecular weight of the silsesquioxane compound of the present invention is not particularly limited. The weight average molecular weight is preferably 1,000 to 100,000, and more preferably 1,000 to 10,000. These ranges are significant in terms of the heat resistance of coating films obtained from the silsesquioxane compound of the present invention, and the viscosity and application properties of active energy ray-curable compositions comprising the silsesquioxane compound of the present invention.

In the present specification, the weight average molecular weight is a value determined by converting the weight average molecular weight measured by gel permeation chromatography ("HLC8120GPC" produced by Tosoh Corporation), based on the weight average molecular weight of polystyrene. Measurements were conducted using the four columns "TSKgel G-4000 HXL", "TSKgel G-3000 HXL", "TSKgel G-2500 HXL" and "TSKgel G-2000 HXL" (trade names; produced by Tosoh Corporation) under the following conditions: mobile phase: tetrahydrofuran; measurement temperature: 40° C.; flow rate: 1 ml/min.; and detector: $R^1$.

Method of Producing Silsesquioxane Compound of the Present Invention

The silsesquioxane compound of the present invention may be produced by various methods. For example, the compound may be produced by the method shown in the following production method A or B.

Production Method A

For example, the production method A is carried out using a starting material containing a hydrolyzable silane having an organic group that is directly attached to a silicon atom and has one or more urethane bonds and one (meth)acryloyloxy group.

Specifically, the silsesquioxane compound of the present invention is produced, for example, by hydrolysis condensation of the starting material using a hydrolyzable silane represented by the formula (IV) below, and optionally, a hydrolyzable silane other than the hydrolyzable silane represented by the formula (IV) below, in the presence of a catalyst.

$$R^6SiX_3 \quad (IV)$$

$R^6$ in the formula (IV) is an organic group having one or more urethane bonds and one (meth)acryloyloxy group. X is the same or different, and each represents chlorine or a $C_{1-6}$ alkoxy group.

Examples of $C_{1-4}$ alkoxy groups include $C_{1-6}$ (preferably $C_{1-4}$) straight or branched alkoxy groups. Specifically, methoxy, ethoxy, n-propoxy, isopropoxy, n-butoxy, isobutoxy, tert-butoxy, sec-butoxy, n-pentyloxy, 1-ethylpropoxy, isopentyloxy, neopentyloxy, n-hexyloxy, 1,2,2-trimethyl propoxy, 3,3-dimethylbutoxy, 2-ethylbutoxy, isohexyloxy, 3-methyl pentyloxy, etc., are included.

Accordingly, specific examples of X include chlorine, methoxy, ethoxy, propoxy, butoxy, etc.

Hydrolyzable silanes other than those represented by the formula (IV) are not particularly limited as long as they are capable of producing a silsesquioxane compound through hydrolysis condensation with the hydrolyzable silane represented by the formula (IV). Specific examples thereof include methyltrimethoxysilane, methyltriethoxysilane, ethyltrimethoxysilane, ethyltriethoxysilane, and like alkyltrialkoxysilanes.

The hydrolyzable silane represented by the formula (IV) can be obtained by reacting, for example, isocyanate-containing trialkoxysilane and hydroxy-containing (meth)acrylic acid ester.

Specific examples of hydrolyzable silanes represented by the formula (IV) include those represented by the formula (V):

[Chem. 12]

$$\text{(V)}$$

$$H_2C=C(R^1)-C(=O)-O-(R^2-O)_{n+1}-C(=O)-NH-R^3-SiX_3$$

wherein $R^1$, $R^2$, $R^3$, n, and X are as defined above.

The hydrolyzable silane represented by the formula (V) can be obtained by reacting, for example, a hydrolyzable silane represented by the formula (VI) and a compound represented by the formula (VII):

[Chem. 13]

$$OCN-R^3-SiX_3 \quad (VI)$$

wherein $R^3$ and X are as defined above, and

[Chem. 14]

$$\text{(VII)}$$

$$H_2C=C(R^1)-C(=O)-O-(R^2-O)_{n+1}-H$$

wherein $R^1$, $R^2$, and n are as defined above.

Examples of compounds represented by the formula (VI) include 3-isocyanate propyltrimethoxysilane, 3-isocyanatepropyl triethoxysilane, and the like.

Examples of compounds represented by the formula (VII) include 2-hydroxyethyl(meth)acrylate, 2-hydroxypropyl (meth)acrylate, 3-hydroxypropyl(meth)acrylate, 4-hydroxybutyl(meth)acrylate, diethyleneglycol mono(meth)acrylate, triethyleneglycol mono(meth)acrylate, dipropyleneglycol mono(meth)acrylate, and the like.

The reaction of the hydrolyzable silane represented by the formula (VI) and the compound represented by the formula (VII) can be performed according to an ordinary method of reacting an isocyanate group and a hydroxy group.

The proportion of the hydrolyzable silane represented by the formula (VI) and the compound represented by the formula (VII) used in the above reaction scheme is such that the latter is about 0.90 to about 1.10 mol, and preferably about 0.95 to about 1.05 mol, per mol of the former.

The reaction temperature is 0 to 200° C., preferably 20 to 200° C., and more preferably 20 to 120° C. The reaction can be performed at any pressure; however, the pressure is preferably in the range of 0.02 to 0.2 MPa, and particularly, 0.08 to 0.15 MPa. The reaction usually completes in about 2 to about 10 hours.

In the reaction, catalysts may be suitably used. Examples of catalysts include tertiary amines such as triethylamine, organic metal compounds such as dibutyltin dilaurate, and the like.

In the reaction, solvents may be suitably used. Examples of solvents include acetone, methyl ethyl ketone, methyl isobutyl ketone, cyclohexanone, methyl amyl ketone, ethyl isoamyl ketone, diisobutyl ketone, methyl hexyl ketone, and like ketones; ethyl acetate, butyl acetate, methyl benzoate, methyl propionate, and like esters; tetrahydrofuran, dioxane, dimethoxyethane, and like ethers; propylene-glycol-monomethyl-ether acetate, 3-methoxy butyl acetate, and like glycol ethers; toluene, xylene, and like aromatic hydrocarbons; aliphatic hydrocarbons; and the like.

Examples of hydrolyzable silanes other than those represented by the formula (IV) include hydrolyzable silanes represented by the formula (VIII) or (IX):

[Chem. 15]

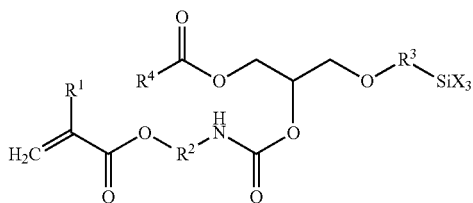

(VIII)

wherein $R^1$, $R^2$, $R^3$, $R^4$, and X are as defined above, and

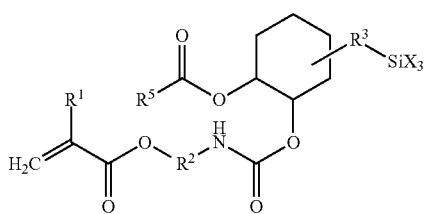

(IX)

wherein $R^1$, $R^2$, $R^3$, $R^5$, and X are as defined above.

The hydrolyzable silane represented by the formula (VIII) can be obtained, for example, by reacting a hydrolyzable silane represented by the formula (X) with a compound represented by the formula (XI), thereby yielding a product, and by further reacting a compound represented by the formula (XII) with the product:

[Chem. 17]

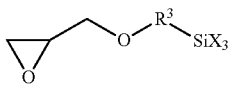

(X)

wherein $R^3$ and X are as defined above,

[Chem. 18]

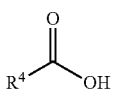

(XI)

wherein $R^4$ is as defined above, and

[Chem. 19]

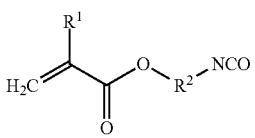

(XII)

wherein $R^1$ and $R^2$ are as defined above.

Examples of hydrolyzable silanes represented by the formula (X) include 3-glycidoxypropyltrimethoxysilane, 3-glycidoxypropyltriethoxysilane, and the like.

Examples of compounds represented by the formula (XI) include acetic acid, propionic acid, butyric acid, valeric acid, caproic acid, enanthic acid, trifluoroacetic acid, 3,3,3-trifluoropropionic acid, etc.

Examples of compounds represented by the formula (XII) include isocyanatemethyl(meth)acrylate, 2-isocyanateethyl(meth)acrylate, 3-isocyanatepropyl(meth)acrylate, isocyanateoctyl(meth)acrylate, etc.

The hydrolyzable silane represented by the formula (IX) can be obtained, for example, by reacting a hydrolyzable silane represented by the formula (XIII) with a compound represented by the formula (XIV), thereby yielding a product, and by further reacting a compound represented by the formula (XV) with the product:

[Chem. 20]

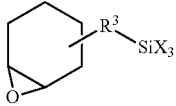

(XIII)

wherein $R^3$ and X are as defined above,

[Chem. 21]

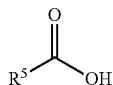
(XIV)

wherein R⁵ is as defined above, and

[Chem. 22]

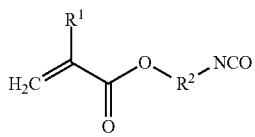
(XV)

wherein R¹ and R² are as defined above.

Examples of hydrolyzable silanes represented by the formula (XIII) include 2-(3,4-epoxycyclohexyl)ethyltrimethoxysilane, 2-(3,4-epoxycyclohexyl)ethyltriethoxysilane, and the like.

As the compound represented by the formula (XIV), compounds listed in the description of the compound represented by the formula (XI) can be used.

As the compound represented by the formula (XV), compounds listed in the description of the compound represented by the formula (XII) can be used.

The reaction of the hydrolyzable silane represented by the formula (X) and the compound represented by the formula (XI), and the reaction of the hydrolyzable silane represented by the formula (XIII) and the compound represented by the formula (XIV) can be carried out according to an ordinary method of reacting a carboxy group and an epoxy group.

The proportion of the hydrolyzable silane represented by the formula (X) and the compound represented by the formula (XI) used in the reaction is such that the latter is about 0.80 to about 1.20 mol, and preferably about 0.90 to about 1.10 mol, per mol of the former.

The proportion of the compound represented by the formula (XIII) and the compound represented by the formula (XIV) is such that the latter is about 0.80 to about 1.20 mol, and preferably about 0.90 to about 1.10 mol, per mol of the former.

The reaction temperature is, for example, 0 to 200° C., preferably 20 to 200° C., and more preferably 20 to 120° C. The reaction generally completes in about 10 to about 24 hours.

In the reaction, catalysts may be used. Specific examples of catalysts include tertiary amines such as triethylamine and benzyldimethylamine; quaternary ammonium salts such as tetramethylammonium chloride, tetraethylammonium bromide, and tetrabutylammonium bromide; secondary amine salts such as acetate and formate of diethylamine etc.; alkali metal or alkaline earth metal hydroxides such as sodium hydroxide and calcium hydroxide; alkali metal or alkaline earth metal salts such as sodium acetate and calcium acetate; imidazoles; cyclic nitrogen-containing compounds such as diazabicycloundecene; phosphorus compounds such as triphenylphosphine and tributylphosphine; and the like. The amount of the catalyst used is not limited, but is specifically, for example, 0.01 to 5 mass % based on the amount of the reaction starting material.

In the reaction, solvents may be suitably used. Solvents are not particularly limited and examples thereof include acetone, methyl ethyl ketone, methyl isobutyl ketone, cyclohexanone, methyl amyl ketone, ethyl isoamyl ketone, diisobutyl ketone, methyl hexyl ketone, and like ketones; ethyl acetate, butyl acetate, methyl benzoate, methyl propionate, and like esters; tetrahydrofuran, dioxane, dimethoxyethane, and like ethers; ethylene-glycol-monamethyl-ether, ethylene-glycol-monoethyl-ether, diethylene-glycol-monomethyl-ether, propylene-glycol-monomethyl-ether acetate, 3-methoxy butyl acetate, and like glycol ethers; toluene, xylene, and like aromatic hydrocarbons; aliphatic hydrocarbons; and the like.

The reaction of the compound represented by the formula (XII) with the reaction product (hereinafter sometimes simply referred to as reaction product (X-XI)) that is obtained by reacting the hydrolyzable silane represented by the formula (X) and the compound represented by the formula (XI), and the reaction of the compound represented by the formula (XV) with the reaction product (hereinafter sometimes simply referred to as reaction product (XIII-XIV)) that is obtained by reacting the hydrolyzable silane represented by the formula (XIII) and the compound represented by the formula (XIV) can be carried out according to an ordinary method of reacting a hydrolyzable group and an isocyanate group.

The proportion of the reaction product (X-XI) and the compound represented by the formula (XII) used in the above reaction is such that the latter is about 0.90 to about 1.10 mol, and preferably about 0.95 to about 1.05 mol, per mol of the former.

The proportion of the reaction product (XIII-XIV) and the compound represented by the formula (XV) used in the above reaction is such that the latter is about 0.90 to about 1.10 mol, and preferably about 0.95 to about 1.05 mol, per mol of the former.

The reaction temperature is, for example, 0 to 200° C., preferably 20 to 200° C., and more preferably 20 to 120° C. The reaction can be carried out at any pressure; however, the pressure is preferably in the range of 0.02 to 0.2 MPa, and more preferably in the range of 0.08 to 0.15 MPa. The reaction generally completes in about 2 to about 10 hours.

In the reaction, catalysts may be suitably used. Examples of the catalysts include tertiary amines such as triethylamine; organic metal compounds such as dibutyltin dilaurate; and the like.

In the reaction, solvents may be suitably used. Examples of solvents include acetone, methyl ethyl ketone, methyl isobutyl ketone, cyclohexanone, methyl amyl ketone, ethyl isoamyl ketone, diisobutyl ketone, methyl hexyl ketone, and like ketones; ethyl acetate, butyl acetate, methyl benzoate, methyl propionate, and like esters; tetrahydrofuran, dioxane, dimethoxyethane, and like ethers; propylene-glycol-monomethyl-ether acetate, 3-methoxy butyl acetate, and like glycol ethers; toluene, xylene, and like aromatic hydrocarbons; aliphatic hydrocarbons; and the like.

In the method of producing the invention, the silsesquioxane compound of the present invention is specifically obtained as follows:

[1] The hydrolyzable silane represented by the formula (IV) is used as a starting material and subjected to hydrolysis condensation in the presence of a catalyst, or

[2] the hydrolyzable silane represented by the formula (IV) and other hydrolyzable silanes are used as starting materials and subjected to hydrolysis condensation in the presence of a catalyst.

As the catalyst, a basic catalyst is preferably used. Specific examples of basic catalysts include alkali metal hydroxides such as potassium hydroxide, sodium hydroxide, and cesium hydroxide; ammonium hydroxide salts such as tetramethylammonium hydroxide, tetraethylammonium hydroxide, tetrabutylammonium hydroxide, and benzyl trimethylammonium hydroxide; ammonium fluoride salts such as tetrabutylammonium fluoride; and the like.

Although the amount of the catalyst used is not limited, using an overly large amount of the catalyst results in high costs, and difficulties in removing the catalyst, while using an overly small amount of the catalyst slows the reaction. Therefore, the amount of the catalyst is preferably 0.0001 to 1.0 mol, and more preferably 0.0005 to 0.1 mol, per mol of hydrolyzable silane.

When the hydrolysis condensation reaction is carried out (the above process [1] or [2]), water is used. The proportion of hydrolyzable silane to water is not limited. The amount of water used is preferably 0.1 to 100 mol, and more preferably 0.5 to 3 mol, per mol of hydrolyzable silane. When the amount of water is too low, the reaction proceeds slowly, possibly resulting in a reduced yield of the target silsesquioxane compound. Conversely, when the amount of water is too high, the molecular weight of the resulting product is increased, possibly resulting in a reduced amount of product having the desired structure. Moreover, when a basic catalyst is used in the form of an aqueous solution, the water used in the reaction may be substituted by the solution, or water may be further added.

In the above hydrolysis condensation reaction, an organic solvent may or may not be used. The use of an organic solvent is preferred in terms of preventing gelation and controlling viscosity during production. As the organic solvent, a polar organic solvent and a nonpolar organic solvent may be used alone or as a mixture thereof.

Examples of polar organic solvents include lower alcohols such as methanol, ethanol, and 2-propanol; ketones such as acetone, and methyl isobutyl ketone; and ethers such as tetrahydrofuran. Particularly, acetone and tetrahydrofuran are preferred because they have a low boiling point, and their use results in a homogeneous system and improved reactivity. Preferred examples of nonpolar organic solvents include hydrocarbon-based solvents; toluene, xylene, and like organic solvents that have a boiling point higher than that of water are more preferred; and toluene and like organic solvents that are azeotroped with water are particularly preferred because water can be efficiently removed from the system. Particularly, a mixture of a polar organic solvent and a nonpolar organic solvent is preferably used because the aforementioned advantages of both solvents can be achieved.

The temperature in the hydrolysis condensation reaction is 0 to 200° C., preferably 10 to 200° C., and more preferably 10 to 120° C. Although this reaction can be carried out at any pressure, the pressure is preferably in the range of 0.02 to 0.2 MPa, and more preferably in the range of 0.08 to 0.15 MPa. The reaction usually completes in about 1 to about 12 hours.

In the hydrolysis condensation reaction, the condensation reaction proceeds with the hydrolysis reaction. In terms of liquid stability, it is preferred that most of the hydrolyzable groups in the hydrolyzable silane (for example, Xs in the formula (IV)), and preferably 100% of the Xs, are hydrolyzed into hydroxyl groups (OH groups), and that most of the OH groups, preferably 80% or higher, more preferably 90% or higher, and even more preferably 100% of the OH groups, are condensed.

After the hydrolysis condensation reaction, the solvent, alcohol produced by the reaction, and catalyst may be removed from the mixture by a known technique. The obtained product may be further purified by removing the catalyst using various purification methods (e.g., washing, column separation, and solid absorbent), depending on the purpose. Preferably, in terms of efficiency, the catalyst is removed by washing with water.

The silsesquioxane compound of the present invention is produced by the above-described production method.

When not all of the OH groups are condensed in the hydrolysis condensation reaction, the product obtained by the production method of the present invention may contain, other than the silsesquioxane compound having a structure in which all of the Si—OH (hydroxysilyl) groups have been subjected to hydrolysis condensation, silsesquioxane compounds having a rudder structure, an incomplete cage structure, and/or a random structure, in which the Si—OH groups remain. The silsesquioxane compound of the present invention obtained by the production method of the present invention may contain such compounds having a rudder structure, an incomplete cage structure, and/or a random structure.

Production Method B

For example, the production method B comprises step B1 of producing a silsesquioxane compound having an epoxy group using a hydrolyzable silane having an epoxy group, step B2 of reacting the carboxyl group of a compound having a carboxyl group with the epoxy group contained in the silsesquioxane compound obtained in step B1, thereby producing a silsesquioxane compound having a secondary hydroxyl group, and step B3 of reacting the isocyanate group of a compound having a (meth)acryloyloxy group and an isocyanate group with the secondary hydroxy group in the silsesquioxane compound obtained in step B2.

Step B1

Examples of epoxy group-containing hydrolyzable silanes used in step B1 include hydrolyzable silanes represented by the formula (XVI) or (XVII) below.

[Chem. 23]

(XVI)

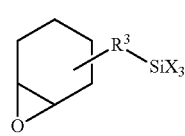

(XVII)

In the formulae (XVI) and (XVII), $R^3$ and X are as defined above.

In step B1, a silsesquioxane compound having an epoxy group is specifically obtained as follows:

[3] The hydrolyzable silanes represented by the formula (XVI) and/or the formula (XVII) are used as starting materials, and subjected to hydrolysis condensation in the presence of a catalyst; or

[4] The hydrolyzable silanes represented by the formula (XVI) and/or the formula (XVII), and hydrolyzable silanes other than those having an epoxy group are subjected to hydrolysis condensation in the presence of a catalyst.

Hydrolyzable silanes other than the aforementioned epoxy group-containing hydrolyzable silanes are not particularly limited as long as they are capable of producing a silsesquioxane compound through hydrolysis condensation with an epoxy group-containing hydrolyzable silane. Specific examples thereof include alkyltrialkoxysilanes such as methyltrimethoxysilane, methyltriethoxysilane, ethyltrimethoxysilane, ethyltriethoxysilane, and the like.

As the catalyst, a basic catalyst is preferably used. Specific examples of basic catalysts include alkali metal hydroxides such as potassium hydroxide, sodium hydroxide, and cesium hydroxide; ammonium hydroxide salts such as tetramethylammonium hydroxide, tetraethylammonium hydroxide, tetrabutylammonium hydroxide, and benzyl trimethylammonium hydroxide; ammonium fluoride salts such as tetrabutylammonium fluoride; and the like.

Although the amount of the catalyst used is not limited, using an overly large amount of the catalyst results in high costs and difficulties in removing the catalyst, while using an overly small amount of the catalyst slows the reaction. Therefore, the amount of the catalyst used is preferably 0.0001 to 1.0 mol, and more preferably 0.0005 to 0.1 mol, per mol of hydrolyzable silane.

When the hydrolysis condensation reaction is carried out (the above process [3] or [4]), water is used. The proportion of hydrolyzable silane and water is not particularly limited. The amount of water used is preferably 0.1 to 100 mol, and more preferably 1.5 to 3 mol, per mol of hydrolyzable silane. When the amount of water is too low, the reaction proceeds slowly, possibly resulting in a reduced yield of the target silsesquioxane. Conversely, when the amount of water is too high, the molecular weight of the resulting product is increased, possibly resulting in a reduced amount of product having the desired structure. Moreover, when a basic catalyst is used in the form of an aqueous solution, the water used in the reaction may be substituted by the solution, or water may be further added.

In the above hydrolysis condensation reaction, an organic solvent may or may not be used. The use of an organic solvent is preferred in terms of preventing gelation and controlling viscosity during production. As the organic solvent, a polar organic solvent and a nonpolar organic solvent may be used alone or as a mixture thereof.

Examples of polar organic solvents include lower alcohols such as methanol, ethanol, and 2-propanol; ketones such as acetone and methyl isobutyl ketone; and ethers such as tetrahydrofuran. Particularly, acetone and tetrahydrofuran are preferred because they have a low boiling point, and the use thereof results in a homogeneous system and improved reactivity. Preferred examples of nonpolar organic solvents include hydrocarbon-based solvents; toluene, xylene, and like organic solvents that have a boiling point higher than that of water are more preferred; and toluene and like organic solvents that are azeotroped with water are particularly preferred because water can be efficiently removed from the system. Particularly, a mixture of a polar organic solvent and a nonpolar organic solvent is preferably used because the aforementioned advantages of both solvents can be achieved.

The temperature in the hydrolysis condensation reaction is 0 to 200° C., preferably 10 to 200° C., and more preferably 10 to 120° C. The reaction usually completes in about 1 to about 12 hours.

In the hydrolysis condensation reaction, the condensation reaction proceeds with the hydrolysis reaction. In terms of liquid stability, it is preferred that most of the Xs in the formulae (XVI) or (XVII), and preferably 100% of the Xs, are hydrolyzed into hydroxyl (OH) groups, and that most of the OH groups, preferably 80% or higher, more preferably 90% or higher, and even more preferably 100% of the OH groups, are condensed.

Step B2

In step B2, a silsesquioxane compound that has organic groups represented by the formula (XX) as organic groups directly attached to a silicon atom is produced by reacting a compound represented by the formula (XIX) with the silsesquioxane compound obtained in step B1 that has organic groups represented by the formula (XVIII) as organic groups directly attached to a silicon atom.

[Chem. 24]

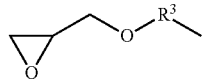
(XVIII)

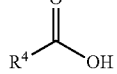
(XIX)

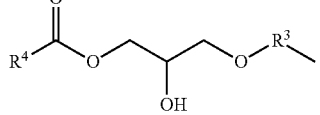
(XX)

In the formulae (XVIII), (XIX), and (XX), $R^3$ and $R^4$ are as defined above.

As another example, a silsesquioxane compound that has organic groups represented by the formula (XXIII) as organic groups directly attached to a silicon atom is produced by reacting a compound represented by the formula (XXII) with the silsesquioxane compound obtained in step B1 that has organic groups represented by the formula (XXI) as organic groups directly attached to a silicon atom.

[Chem. 25]

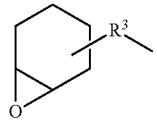
(XXI)

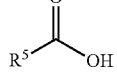
(XXII)

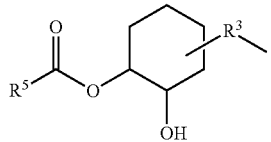
(XXIII)

In the formulae (XXI), (XXII), and (XXIII), $R^3$ and $R^5$ are as defined above.

The reaction for producing the silsesquioxane compound that has an organic group represented by the formula (XX) as an organic group directly attached to a silicon atom, and the reaction for producing the silsesquioxane compound that has an organic group represented by the formula (XXIII) as an organic group directly attached to a silicon atom can be carried out according to an ordinary method of reacting an epoxy group and a carboxyl group.

The reaction temperature is 0 to 200° C., preferably 20 to 200° C., and more preferably 20 to 120° C. The reaction usually completes in about 10 to about 24 hours.

In the above reaction, the proportion of the compound represented by the formula (XIX) and the silsesquioxane compound including the organic group represented by the formula (XVIII) is such that the compound represented by the formula (XIX) is contained in an amount of about 0.80 to about 1.20 mol, and preferably about 0.90 to about 1.10 mol, per mol of the organic group represented by the formula (XVIII) in the silsesquioxane compound.

In the above reaction, the proportion of the compound represented by the formula (XXII) and the silsesquioxane compound including the organic group represented by the formula (XXI) is such that the compound represented by the formula (XXII) is contained in an amount of about 0.80 to about 1.20 mol, and preferably about 0.80 to about 1.20 mol, per mol of the organic group represented by the formula (XXI) in the silsesquioxane compound.

In the reaction, catalysts may be suitably used. Specific examples of catalysts include tertiary amines such as triethylamine and benzyldimethylamine; quaternary ammonium salts such as tetramethylammonium chloride, tetraethylammonium bromide, and tetrabutylammonium bromide; secondary amine salts such as acetate and formate of diethylamine etc.; alkali metal or alkaline earth metal hydroxides such as sodium hydroxide and calcium hydroxide; alkali metal or alkaline earth metal salts such as sodium acetate and calcium acetate; imidazoles; cyclic nitrogen-containing compounds such as diazabicycloundecene; phosphorus compounds such as triphenylphosphine and tributylphosphine; and the like. The amount of the catalyst used is not limited, but is specifically, for example, 0.01 to 5 mass % based on the amount of the reaction starting material.

In the reaction, solvents may be suitably used. Solvents are not particularly limited and examples thereof include acetone, methyl ethyl ketone, methyl isobutyl ketone, cyclohexanone, methyl amyl ketone, ethyl isoamyl ketone, diisobutyl ketone, methyl hexyl ketone, and like ketones; ethyl acetate, butyl acetate, methyl benzoate, methyl propionate, and like esters; tetrahydrofuran, dioxane, dimethoxyethane, and like ethers; ethylene-glycol-monomethyl-ether, ethylene-glycol-monoethyl-ether, diethylene-glycol-monomethyl-ether, propylene-glycol-monomethyl-ether acetate, 3-methoxy butyl acetate, and like glycol ethers; toluene, xylene, and like aromatic hydrocarbons; aliphatic hydrocarbons; and the like.

Step B3

In step B3, a compound represented by the formula (XXIV) is reacted with the silsesquioxane compound obtained in step B2 that has the organic group represented by the formula (XX) as an organic group directly attached to a silicon atom.

[Chem. 26]

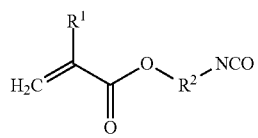

(XXIV)

In the formula (XXIV), $R^1$ and $R^2$ are as defined above.

By this reaction, the silsesquioxane compound that has organic groups represented by the formula (II) as organic groups directly attached to a silicon atom can be obtained.

As another example, the compound represented by the formula (XXV) is reacted with the silsesquioxane compound obtained in step B2 that has organic groups represented by the formula (XXIII) as organic groups directly attached to a silicon atom.

[Chem. 27]

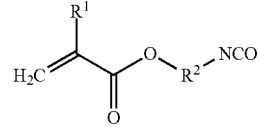

(XXV)

In the formula (XXV), $R^1$ and $R^2$ are as defined above.

By this reaction, a silsesquioxane compound having an organic group represented by the formula (III) as an organic group directly attached to a silicon atom can be obtained.

The reaction can be carried out according to an ordinary method of reacting a hydroxyl group and an isocyanate group. The reaction temperature is 0 to 200° C., preferably 10 to 200° C., and more preferably 10 to 120° C. The reaction usually completes in about 2 to about 10 hours.

In the reaction, the proportion of the compound represented by the formula (XXIV) and the silsesquioxane compound including the organic group represented by the formula (XX) is such that the compound represented by the formula (XXIV) is contained in an amount of about 0.90 to about 1.10 mol, and preferably about 0.95 to about 1.05 mol, per mol of the organic group represented by the formula (XX) in the silsesquioxane compound.

In the reaction, the proportion of the compound represented by the formula (XXV) and the silsesquioxane compound including the organic group represented by the formula (XXIII) is such that the compound represented by the formula (XXV) is contained in an amount of about 0.90 to about 1.10 mol, and preferably about 0.95 to about 1.05 mol, per mol of the organic group represented by the formula (XXIII) in the silsesquioxane compound.

In the reaction, catalysts may be suitably used. Examples of catalysts include tertiary amines such as triethylamine; organic metal compounds such as dibutyltin dilaurate; and the like.

The silsesquioxane compound of the present invention can be produced according to the production method described above.

The target compound obtained by the aforementioned reaction is separated from the system by general separation means, and can be further purified. Separation and purification are performed, for example, by way of evaporation, solvent extraction, dilution, recrystallization, column chromatography, ion-exchange chromatography, gel chromatography, affinity chromatography, etc.

When not all of the OH groups are condensed in the hydrolysis condensation reaction in step B1, the product obtained by the production method B may contain, other than a silsesquioxane compound having a structure in which all of the Si—OH groups are subjected to hydrolysis condensation, silsesquioxane compounds having a rudder structure, an incomplete cage structure, and/or a random structure, in which the Si—OH groups remain. The silsesquioxane compound of the present invention obtained by the production method B may contain such compounds having a rudder structure, an incomplete cage structure, and/or a random structure.

Active Energy Ray-Curable Composition

The active energy ray-curable composition of the present invention comprises the silsesquioxane compound of the present invention and a photoinitiator.

Photoinitiator

There is no particular limitation to the usable photoinitiators, as long as they absorb an active energy ray and generate a radical.

Examples of the photoinitiators include benzyl, diacetyl, and like α-diketones; benzoin and like acyloins; benzoin methyl ether, benzoin ethyl ether, benzoin isopropyl ether, and like acyloin ethers; thioxanthone, 2,4-diethylthioxanthone, 2-isopropylthioxanthone, thioxanthone-4-sulfonic acid, and like thioxanthones; benzophenone, 4,4'-bis(dimethylamino)benzophenone, 4,4'-bis(diethylamino)benzophenone, and like benzophenones; Michler's ketones; acetophenone, 2-(4-toluenesulfonyloxy)-2-phenylacetophenone, p-dimethylaminoacetophenone, α,α'-dimethoxyacetoxybenzophenone, 2,2'-dimethoxy-2-phenylacetophenone, p-methoxyacetophenone, 2-methyl[4-(methylthio)phenyl]-2-morpholino-1-propanone, 2-benzyl-2-dimethylamino-1-(4-morpholinophenyl)-butan-1-one, α-isohydroxy isobutylphenone, α,α'-dichloro-4-phenoxyacetophenone, 1-hydroxy-cyclohexyl-phenyl-ketone, and like acetophenones; 2,4,6-trimethylbenzoyldiphenylphosphine oxide, bis(acyl)phosphine oxide, and like acylphosphine oxides; anthraquinone, 1,4-naphthoquinone, and like quinones; phenacyl chloride, trihalomethylphenylsulfone, tris(trihalomethyl)-s-triazine, and like halogenated compounds; di-t-butyl peroxide, and like peroxides; etc. These may be used singly, or in a combination of two or more.

Examples of commercially available photoinitiators include Irgacure 184, Irgacure 261, Irgacure 500, Irgacure 651, Irgacure 907, and Irgacure CGI 1700 (trade names, products of Ciba Specialty Chemicals); Darocur 1173, Darocur 1116, Darocur 2959, Darocur 1664, Darocur 4043 (trade names, products of Merck Japan Ltd.); Kayacure-MBP, Kayacure-DETX-S, Kayacure-DMBI, Kayacure-EPA, Kayacure-OA (trade names, products of Nippon Kayaku Co., Ltd.); Vicure 10, Vicure 55 (trade names, products of Stauffer Co., Ltd.); Trigonal P1 (trade name, a product of Akzo Co., Ltd.); Sandoray 1000 (trade name, a product of Sandoz Co., Ltd.); Deap (trade name, a product of APJOHN Co., Ltd.); Quantacure PDO, Quantacure ITX, Quantacure EPD (trade names, products of Ward Blenkinsop Co., Ltd.); etc.

From the viewpoint of photocurability, the photoinitiator preferably comprises at least one of thioxanthones, acetophenones and acyl phosphine oxides, or a mixture thereof. Of these, the photoinitiator more preferably comprises a mixture of acetophenones and acyl phosphine oxides.

The amount of the photoinitiator used is not particularly limited, but is preferably within a range of from 0.5 to 10 parts by mass, and more preferably within a range of from 1 to 5 parts by mass, per 100 parts by mass of the total amount of nonvolatile components in the active energy ray-curable composition. The lower limit of the above range is important to improve the curability with an active energy ray, and the upper limit is important in terms of the cost and deep-section curability.

The proportion of the silsesquioxane compound of the present invention to a photoinitiator is not particularly limited, but the photoinitiator is generally used in an amount of 1 to 20 parts by mass, preferably 2 to 10 parts by mass, per 100 parts by mass of nonvolatile components of the silsesquioxane compound.

Polymerizable Unsaturated Compound

The active energy ray-curable composition of the present invention may further comprise a polymerizable unsaturated compound. There is no particular limitation to the usable polymerizable unsaturated compounds, as long as the polymerizable unsaturated compound is a compound other than the silsesquioxane compound of the present invention and has at least one polymerizable unsaturated double bond in its chemical structure.

Examples of the polymerizable unsaturated compounds include esterified products of a monohydric alcohol and (meth)acrylic acid, and the like. Specific examples thereof include methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, neopentyl (meth)acrylate, cyclohexyl (meth)acrylate, tetrahydrofurfuryl (meth)acrylate, isobornyl (meth)acrylate, phenyl (meth)acrylate, benzyl (meth)acrylate, N-acryloyloxyethyl hexahydrophthalimide, and the like. Examples of the polymerizable unsaturated compounds further include esterified products of a polyhydric alcohol and (meth)acrylic acid. Specific examples thereof include ethylene glycol di(meth)acrylate, diethylene glycol di(meth)acrylate, triethylene glycol di(meth)acrylate, tetraethylene glycol di(meth)acrylate, 1,3-butanediol di(meth)acrylate, 1,4-butanediol di(meth)acrylate, 1,9-nonanediol di(meth)acrylate, glycerin di(meth)acrylate, trimethylolpropane di(meth)acrylate, pentaerythritol di(meth)acrylate, neopentyl glycol di(meth)acrylate, 1,6-hexanediol di(meth)acrylate, pentaerythritol di(meth)acrylate, bisphenol A ethylene oxide-modified di(meth)acrylate, and like di(meth)acrylate compounds; glycerin tri(meth)acrylate, trimethylolpropane tri(meth)acrylate, trimethylolpropane propylene oxide-modified tri(meth)acrylate, trimethylolpropane ethylene oxide-modified tri(meth)acrylate, pentaerythritol tri(meth)acrylate, ε-caprolactone-modified tris (acryloxyethyl)isocyanurate, and like tri(meth)acrylate compounds; pentaerythritol tetra(meth)acrylate, and like tetra(meth)acrylate compounds; and dipentaerythritol penta(meth)acrylate, dipentaerythritol hexa(meth)acrylate, etc. Examples thereof further include urethane (meth)acrylate resins, epoxy (meth)acrylate resins, polyester (meth)acrylate resins, and the like. Urethane (meth)acrylate resins can be obtained by, for example, using a polyisocyanate compound, a hydroxyalkyl (meth)acrylate, and a polyol compound as starting materials, and carrying out a reaction in such a manner that a hydroxyl group is used in an equimolar or excess amount based on the amount of isocyanate. The polymerizable unsaturated compounds can be used singly, or in a combination of two or more.

When used, the amount of the polymerizable unsaturated compound is not particularly limited. However, from the viewpoint of the properties of the formed coating film, the amount of the polymerizable unsaturated compound used is preferably 0.1 to 1,000 parts by mass, and more preferably 20 to 200 parts by mass, per 100 parts by mass of nonvolatile components of the silsesquioxane compound of the present invention.

The active energy ray-curable composition of the present invention may optionally comprise various additives, and may be diluted with a solvent as required. Examples of the additives include sensitizers, UV absorbers, light stabilizers, polymerization inhibitors, antioxidants, defoaming agents, surface control agents, plasticizers, coloring agents, and the like.

Examples of the solvents used for dilution include acetone, methyl ethyl ketone, methyl isobutyl ketone, and like ketones; ethyl acetate, butyl acetate, methyl benzoate, methyl propionate, and like esters; tetrahydrofuran, dioxane, dimethoxyethane, and like ethers; ethylene glycol monomethyl ether, ethylene glycol monoethyl ether, diethylene glycol monomethyl ether, propylene glycol'monomethyl ether acetate, 3-methoxybutyl acetate, and like glycol ethers; and aromatic hydrocarbons and aliphatic hydrocarbons, etc. These can suitably be used in a combination for the purpose of adjusting viscosity, application properties, etc.

There is no particular limitation to the nonvolatile components in the active energy ray-curable composition of the present invention. For example, the amount is preferably 20 to 100 mass %, and more preferably 25 to 70 mass %. The above-mentioned amount range is important in terms of the smoothness of the formed coating film, and to shorten the drying time.

There is no particular limitation to methods for applying the active energy ray-curable composition of the present invention to the surface of a substrate. Examples thereof include roller coating, roll coater coating, spin coater coating, curtain roll coater coating, slit coater coating, spray coating, electrostatic coating, dip coating, silk printing, spin coating, and the like.

The substrates are not particularly limited. Specific examples of the substrates include metal, ceramic, glass, plastic, wood, and the like.

When a coating film is formed from the above-mentioned active energy ray-curable composition, drying may be performed if required. The drying method is not particularly limited insofar as the solvents contained therein can be removed. For example, the drying may be performed at a temperature of 20 to 100° C. for 3 to 20 minutes.

The film thickness of the coating film is arbitrarily adjusted according to the purpose. For example, the film thickness is preferably 1 to 100 μm, and more preferably 1 to 20 μm. If the film thickness is greater than the lower limit of the above-mentioned range, the coating film will have excellent smoothness and appearance. If the film thickness is below the upper limit of the above-mentioned range, the coating film will have excellent curability and cracking resistance.

After the active energy ray-curable composition is applied to the surface of a substrate, an active energy ray is irradiated to form a cured coating film. There is no particular limitation to the radiation source and radiation dose of the active energy-ray irradiation. Examples of radiation sources of an active energy ray include an extra-high pressure mercury-vapor lamp, a high pressure mercury-vapor lamp, a middle pressure mercury-vapor lamp, a low-pressure mercury-vapor lamp, a chemical lamp, a carbon arc light, a xenon light, a metal halide light, a fluorescent light, a tungsten light, sunlight, and the like. The radiation dose is, for example, preferably within a range of from 5 to 20,000 J/m$^2$, and more preferably within a range of from 100 to 10,000 J/m$^2$.

The active energy-ray irradiation can be performed in open air, or in an inert gas atmosphere. Examples of inert gases include nitrogen, carbon dioxide, and the like. From the viewpoint of curability, the active energy-ray irradiation is preferably performed in an inert gas atmosphere.

After the active energy-ray irradiation, the coating film may be heated, if necessary. The heating can alleviate the deformation of the coating film that is caused when the film is cured using the active energy-ray irradiation. Further, the heating may improve the hardness and adhesion of the coating film. The heating can generally be performed at an ambient temperature of 150 to 250° C. for 1 to 30 minutes.

EXAMPLES

The present invention is described in more detail below with reference to Examples. The phrases "parts" and "%" mean "parts by mass" and "t by mass", respectively, unless otherwise stated. The structural analysis and measurement in the Examples were conducted using, in addition to the analysis equipment described above in the specification, the following analysis equipment and measuring method.

$^{29}$Si-NMR Analysis and $^1$H-NMR Analysis
    Equipment: FT-NMR EX-400, manufactured by JEOL
    Solvent: CDCl$_3$
    Internal standard substance: tetramethylsilane FT-IR Analysis
    Equipment: FT/IR-610, manufactured by JASCO Corporation SP Value Measurement Method The SP value used in the Examples is a solubility parameter that can be measured by a simple measurement method (turbidimetric titration), and the value is calculated according to the following formula suggested by K. W. Suh and J. M. Corbett (see the description of Journal of Applied Polymer Science, 12, 2359, 1968).

$$\text{Formula: } SP=(\sqrt{Vml}\cdot\delta H+\sqrt{Vmh}\cdot\delta D)/(\sqrt{Vml}+\sqrt{Vmh})$$

In turbidimetric titration, n-hexane is gradually added into a solution of 0.5 g of a sample dissolved in 10 ml of acetone, and the titration amount H (ml) at the turbidity point is read. Similarly, deionized water is added into an acetone solution, and the titration amount D (ml) at the turbidity point is read. These values are applied to the following formulae to determine Vml, Vmh, δH, and δD. The molecular volume (mol/ml) of each solvent is as follows: acetone: 74.4, n-hexane: 130.3, and deionized water: 18. SP of each solvent is as follows: acetone: 9.75, n-hexane: 7.24, and deionized water: 23.43.

$$Vml=74.4\times130.3/((1-VH)\times130.3+VH\times74.4)$$

$$Vmh=74.4\times18/((1-VD)\times18+VD\times74.4)$$

$$VH=H/(10+H)$$

$$VD=D/(10+D)$$

$$\delta H=9.75\times10/(10+H)+7.24\times H/(10+H)$$

$$\delta D=9.75\times10/(10+D)+23.43\times D/(10+D)$$

Example 1

One hundred parts of 3-isocyanatepropyltriethoxysilane, 47 parts of 2-hydroxyethyl acrylate, and 0.1 parts of methoquinone were placed in a separable flask equipped with a reflux condenser, a thermometer, and a stirrer, and the mixture was reacted at 100° C. for 12 hours while blowing dry air thereinto. Thereby, a product (P1) was obtained. Subsequently, 300 parts of toluene, 30 parts of a tetrabutylammonium hydroxide 40% methanol solution, and 12 parts of deionized water were placed in a separable flask equipped with a reflux condenser, a thermometer, and a stirrer, and the mixture was cooled in an ice bath to 2° C. A solution containing a mixture of 300 parts of tetrahydrofuran and 147 parts of the product (P1) was added thereto to carry out a reaction at 20° C. for 24 hours. Then, volatile components were removed by vacuum distillation, and the resulting product was dissolved in 100 parts of propylene glycol monomethyl ether acetate. Thereby, a product (P2) solution having a nonvolatile content of 50% was obtained.

As a result of $^{29}$Si-NMR analysis of the product (P2), a peak derived from a T3 structure in which all of three oxygen atoms attached to Si were attached to other Si was observed at about −70 ppm, and a peak derived from a T2 structure having a hydroxysilyl group was observed at −59 ppm. The integrated intensity ratio of these peaks, i.e., the peak derived from the T3 structure/the peak derived from T2 structure, was 90/10.

Further, as a result of $^1$H-NMR analysis of the product (P2), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 1.01.

As a result of FT-IR analysis of the product (P2), a peak belonging to a urethane bond was observed at about 1540 cm$^{-1}$.

Further, as a result of gel permeation chromatography (GPC) analysis of the product (P2), the weight average molecular weight was 2,500.

The results of the $^{29}$Si-NMR, $^1$H-NMR, FT-IR, and GPC analyses of the product (P2) demonstrated that the product (P2) was a silsesquioxane compound comprising organic groups each directly attached to a silicon atom, each of the organic groups being represented by Formula (XXVI):

[Chem. 28]

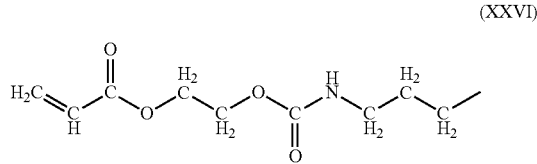

(XXVI)

wherein the silsesquioxane compound comprises 85% or more of a silsesquioxane compound that has a weight average molecular weight of 2,500 and a structure in which all of the Si—OH groups are hydrolyzed and condensed. The obtained silsesquioxane compound had an SP value of 10.5.

Example 2

One hundred parts of 3-isocyanatepropyltriethoxysilane, 58 parts of 4-hydroxybutylacrylate, and 0.1 parts of methoquinone were placed in a separable flask equipped with a reflux condenser, a thermometer, and a stirrer, and the mixture was reacted at 100° C. for 12 hours while blowing dry air thereinto. Thereby, a product (P3) was obtained. Subsequently, 1,000 parts of toluene, 20 parts of deionized water, 147 parts of the product (P3), and 10 parts of a 1N-aqueous hydrochloric acid solution were placed in a separable flask equipped with a reflux condenser, a thermometer, and a stirrer, and the mixture was heated to 60° C. After a reaction was allowed to proceed for 6 hours, the reflux condenser was removed while a water recovery device was installed. Then, water was distilled off while toluene was refluxed at 110° C. After water removal was completed, the toluene was distilled off so that the nonvolatile content in the resulting product was 50%. Thereby, a product (P4) solution having a nonvolatile content of 50% was obtained.

As a result of $^{29}$Si-NMR analysis of the product (P4), a peak derived from a T3 structure in which all of three oxygen atoms attached to Si were attached to other Si was observed at about −70 ppm, and a peak derived from a T2 structure having a hydroxysilyl group was observed at −59 ppm. The integrated intensity ratio of these peaks, i.e., the peak derived from the T3 structure/the peak derived from T2 structure, was 80/20.

Further, as a result of $^1$H-NMR analysis of the product (P4), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 1.02.

As a result of FT-IR analysis of the product (P4), a peak belonging to a urethane bond was observed at about 1540 cm$^1$.

Further, as a result of GPC analysis of the product (P4), the weight average molecular weight was 3,000.

The results of the $^{29}$Si-NMR, $^1$H-NMR, FT-IR, and GPC analyses of the product (P4) demonstrated that the product (P4) was a silsesquioxane compound comprising organic groups each directly attached to a silicon atom, each of the organic groups being represented by Formula (XXVII):

[Chem. 29]

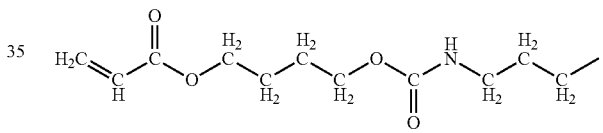

(XXVII)

wherein the silsesquioxane compound comprises 55% or more of a silsesquioxane compound that has a weight average molecular weight of 3,000 and a structure in which all of the Si—OH groups are hydrolyzed and condensed. The obtained silsesquioxane compound had an SP value of 10.4.

Example 3

One hundred parts of Glycidyl POSS Cage Mixture (trade name, manufactured by Hybrid Plastics) and 140 parts of butyl acetate were placed in a separable flask equipped with a reflux condenser, a thermometer, an air-introducing pipe, and a stirrer, and the mixture was stirred at 60° C. until dissolution was complete. Then, 40 parts of acetic acid, 0.5 parts of methoquinone, and 10 parts of tetrabutylammonium bromide were added thereto to carry out a reaction at 120° C. for 12 hours while blowing dry air thereinto. The thus-obtained reaction product was cooled to 80° C., and then, 85 parts of 2-isocyanate ethyl acrylate and 133 parts of butyl acetate were added thereto to carry out a reaction at 80° C. for 10 hours. Thereby, a product (P5) solution having a nonvolatile content of 50% was obtained.

The Glycidyl-POSS Cage Mixture used as a starting material was 3-glycidoxypropyl group-containing cage-type polysilsesquioxane having a weight average molecular weight of 1,800, and an epoxy equivalent of 168 g/eq.

As a result of $^{29}$Si-NMR analysis of the product (P5), only a peak derived from a T3 structure in which all of three oxygen atoms attached to Si were attached to other Si was observed at around −70 ppm, while no peak derived from a T1 or T2 structure indicating the presence of a hydroxysilyl group was observed.

Further, as a result of ¹H-NMR analysis of the product (P5), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 1.00. A peak belonging to an epoxy group was not observed. The epoxy equivalent determined by titration was 10,000 g/eq or more.

Moreover, as a result of FT-IR analysis of the product (P5), a broad peak belonging to a urethane bond, which was not observed in the Glycidyl POSS Cage Mixture (starting material), was observed at around 1540 cm⁻¹.

Further, as a result of GPC analysis of the product (P5), the weight average molecular weight was 4,000.

The results of the ²⁹Si-NMR, ¹H-NMR, FT-IR, and GPC analyses of the product (P5) demonstrated that the product (P5) was a silsesquioxane compound comprising organic groups each directly attached to a silicon atom, each of the organic groups being represented by Formula (XXVIII):

[Chem. 30]

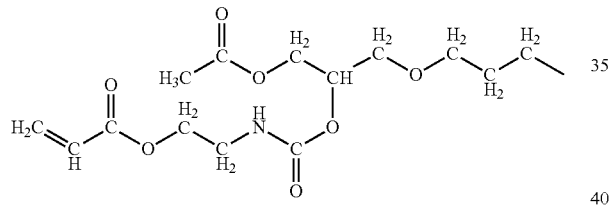

(XXVIII)

wherein the silsesquioxane compound comprises 55% or more of a silsesquioxane compound that has a weight average molecular weight of 4,000 and a structure in which all of the Si—OH groups are hydrolyzed and condensed. The obtained silsesquioxane compound had an SP value of 11.2.

Example 4

Four hundred parts of Epoxycyclohexyl-POSS Cage Mixture (trade name, manufactured by Hybrid Plastics) and 600 parts of propylene glycol monomethyl ether acetate were placed in a separable flask equipped with a reflux condenser, a thermometer, an air-introducing tube, and a stirrer, and the mixture was stirred at 60° C. until dissolution was complete. Then, 136 parts of acetic acid, 1.5 parts of methoquinone, and 10 parts of tetrabutylammonium bromide were added thereto to carry out a reaction at 120° C. for 24 hours while blowing dry air thereinto. The thus-obtained reaction product was cooled to 80° C., and then, 318 parts of 2-isocyanate ethyl acrylate and 440 parts of butyl acetate were added thereto to carry out a reaction at 80° C. for 10 hours. Thereby, a product (P6) solution having a nonvolatile content of 50% was obtained.

The Epoxycyclohexyl-POSS Cage Mixture used as a starting material was 2-(3,4-epoxycyclohexyl)ethyl group-containing cage-type polysilsesquioxane having a weight average molecular weight of 2,200 and an epoxy equivalent of 178 g/eq.

As a result of ²⁹Si-NMR analysis of the product (P6), only a peak derived from a T3 structure in which all of three oxygen atoms attached to Si were attached to other Si was observed at around −70 ppm, while no peak derived from a T1 or T2 structure indicating the presence of a hydroxysilyl group was observed.

Further, as a result of ¹H-NMR analysis of the product (P6), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 1.00. A peak belonging to an epoxy group was not observed. The epoxy equivalent was 10,000 g/eq or more.

As a result of FT-IR analysis of the product (P6), a broad peak belonging to a urethane bond, which was not observed in the Epoxycyclohexyl-POSS Cage Mixture (starting material), was observed at 1540 am⁻¹.

Further, as a result of GPC analysis of the product (P6), the weight average molecular weight was 4,500.

The results of the ²⁹Si-NMR, ¹H-NMR, FT-IR, and GPC analyses of the product (P6) demonstrated that the product (P6) was a silsesquioxane compound comprising organic groups each directly attached to a silicon atom, each of the organic groups being represented by Formula (XXIX):

[Chem. 31]

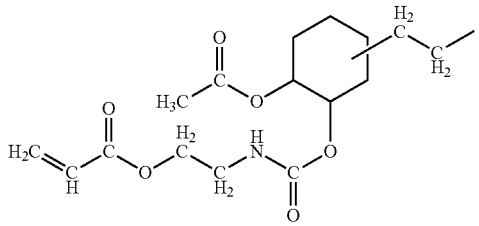

(XXIX)

wherein the silsesquioxane compound comprises 55% or more of a silsesquioxane compound that has a weight average molecular weight of 4,500 and a structure in which all of the Si—OH groups are hydrolyzed and condensed. The obtained silsesquioxane compound had an SP value of 10.6.

Example 5

Five hundred and sixty five parts of 3-glycidoxypropyltrimethoxysilane, 2,260 parts of 2-propanol, 2.0 parts of tetrabutylammonium fluoride, and 65 parts of deionized water were placed in a separable flask equipped with a reflux condenser, a thermometer, and a stirrer, and the mixture was heated to 60° C. by a mantle heater while being stirred under a nitrogen stream. After a reaction was allowed to proceed for 10 hours at 60° C., the water, methanol and 2-propanol were removed by vacuum distillation. Then, 600 parts of propylene glycol monomethyl ether acetate was added to the resulting product to thereby obtain a product (P7) solution having a nonvolatile content of 40%.

Subsequently, 1,000 parts of the product (P7) solution having a nonvolatile content of 40%, 160 parts of acetic acid, 1.5 parts of methoquinone, and 10 parts of tetrabutylammonium bromide were placed in a separable flask equipped with a reflux condenser, a thermometer, and a stirrer, and the mixture was reacted at 100° C. for 24 hours while blowing dry air thereinto. The resulting product was cooled to 80° C., and then, 170 parts of 2-isocyanate ethyl acrylate was added thereto. The resulting mixture was allowed, as is, to undergo a reaction for 10 hours, and the reaction product was diluted with 210 parts of propylene glycol monomethyl ether acetate. Thereby, a product (P8) solution having a nonvolatile content of 50% was obtained.

As a result of $^{29}$Si-NMR analysis of the product (P7), only a peak derived from a T3 structure in which all of three oxygen atoms attached to Si were attached to other Si was observed at around −70 ppm, while no peak derived from a T1 or T2 structure indicating the presence of a hydroxysilyl group was observed.

Further, as a result of $^{1}$H-NMR analysis of the product (P7), a peak derived from a methylene group attached to Si was observed at 0.6 ppm, and peaks derived from an epoxy group were observed at 2.6 ppm, 2.8 ppm, and 3.1 ppm. The molar ratio of the epoxy group to Si determined from the ratio of these peaks was 1.0.

Moreover, as a result of FT-IR analysis of the product (P7), peaks belonging to an Si—O—Si bond were observed at around 1,100 cm$^{-1}$ and around 1,050 cm$^{-1}$. However, almost no peak belonging to the hydroxysilyl group was observed at around 3,500 cm$^{-1}$. A peak belonging to the epoxy group was observed at around 910 cm$^{-1}$. The epoxy equivalent of the product (P7) was 168 g/eq.

Furthermore, as a result of GPC analysis of the product (P7), peaks each having a polystyrene equivalent molecular weight of 2,800, 2,000, or 1,200 were observed. Among these, the largest and sharpest peak having a molecular weight of 1,200 was estimated to belong to an octamer, i.e., a silsesquioxane compound [(RSiO$_{3/2}$)$_8$], and the proportion of this component was 70 mass % of the whole. The weight average molecular weight of the product (P7) was 1,750.

The results of the $^{29}$Si-NMR, $^{1}$H-NMR, FT-IR, and GPC analyses of the product (P7) demonstrated that the product (P7) was a silsesquioxane compound having a weight average molecular weight of 1,750 and comprising 70 mass % or more of a silsesquioxane compound represented by the formula: (R$^{7}$SiO$_{3/2}$)$_8$, wherein R$^{7}$ is a 3-glycidoxypropyl group.

Subsequently, as a result of $^{29}$Si-NMR analysis of the product (P8), only a peak belonging to the T3 structure was observed at around −70 ppm.

Further, as a result of $^{1}$H-NMR analysis of the product (P8), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 0.50. The peak derived from the epoxy group that was observed in the analysis of the product (P7) disappeared. The epoxy equivalent was 10,000 g/eq or more, and the NCO value was 0.

Moreover, as a result of FT-IR analysis of the product (P8), a broad peak belonging to a hydroxyl group, which was not observed in the analysis of the product (P7), was observed at around 3500 am$^{-1}$, and a broad peak belonging to a urethane bond was observed at around 1540 cm$^{-1}$ Furthermore, as a result of GPC analysis of the product (P8), the weight average molecular weight was 3,600.

The results of the $^{29}$Si-NMR, $^{1}$H-NMR, FT-IR, and GPC analyses of the product (P8) demonstrated that the product (P8) was a silsesquioxane compound comprising organic groups, each directly attached to a silicon atom, 50 mol % of the organic groups being represented by Formula (XXVIII), and 50 mol % of the organic groups being represented by Formula (XXX),

[Chem. 32]

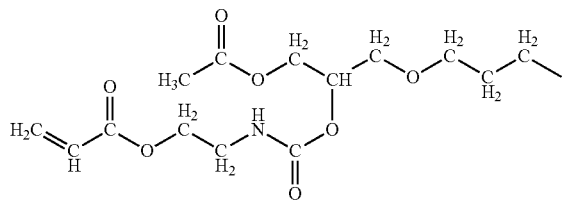

(XXVIII)

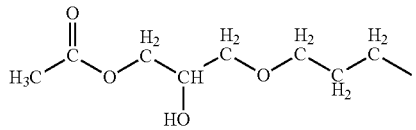

(XXX)

wherein the silsesquioxane compound comprises 70% or more of a silsesquioxane compound that has a weight average molecular weight of 3,600 and a structure in which all of the Si—OH groups are hydrolyzed and condensed. The obtained silsesquioxane compound had an SP value of 11.7.

Comparative Example 1

Three hundred parts of toluene, 30 parts of a tetrabutylammonium hydroxide 40% methanol solution, and 12 parts of deionized water were placed in a separable flask equipped with a reflux condenser, a thermometer, and a stirrer, and the mixture was cooled in an ice bath to 2° C. Then, 110 parts of 3-acryloyloxypropyl trimethoxysilane diluted with 300 parts of tetrahydrofuran was added thereto to carry out a reaction at 20° C. for 24 hours. After volatile components were removed by vacuum distillation, the resulting product was dissolved in 100 parts of propylene glycol monomethyl ether acetate. Thereby, a product (P9) solution having a nonvolatile content of 50% was obtained.

As a result of $^{29}$Si-NMR analysis of the product (P9), a peak derived from a T3 structure in which all of three oxygen atoms attached to Si were attached to other Si was observed at around −70 ppm, and a peak derived from a T2 structure having a hydroxysilyl group was observed at −59 ppm. The integrated intensity ratio of these peaks, i.e., the peak derived from the T3 structure/the peak derived from T2 structure, was 90/10.

Further, as a result of $^{1}$H-NMR analysis of the product (P9), a peak derived from a methylene group attached to Si was observed at 0.6 ppm. In addition, peaks derived from the carbon-carbon unsaturated bond of an acryloyloxy group were observed at 5.9 ppm, 6.1 ppm, and 6.4 ppm. Calculations based on the intensity ratio of these peaks showed that the molar ratio of the carbon-carbon unsaturated bond of the acryloyloxy group to the methylene group attached to Si was 1.00.

Furthermore, as a result of GPC analysis of the product (P9), the weight average molecular weight was 1,500.

The results of the $^{29}$Si-NMR, $^1$H-NMR, FT-IR, and GPC analyses of the product (P9) demonstrated that the product (P9) was a silsesquioxane compound comprising organic groups each directly attached to a silicon atom, each of the organic groups being represented by Formula (XXXI):

[Chem. 33]

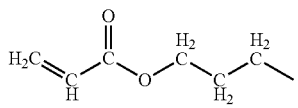

(XXXI)

wherein the silsesquioxane compound comprises 80% or more of a silsesquioxane compound that has a weight average molecular weight of 1,500 and a structure in which all of the Si—OH groups are hydrolyzed and condensed. The obtained silsesquioxane compound had an SP value of 9.5.

Example 6

The product (P2) solution having a nonvolatile content of 50% obtained in Example 1 and a polymerizable unsaturated compound (A1), described later, were mixed so that the mass ratio of the product (P2) to the polymerizable unsaturated compound (A1) was 1:1, and the mixture was stirred at 40° C. for 24 hours to obtain a mixed solution. The mixed solution was assessed to evaluate the compatibility of the product (P2) obtained in Example 1 with the polymerizable unsaturated compound in a solution state. The dissolved state of the mixed solution was visually observed, and evaluated according to the following criteria. Table 1 shows the evaluation results.

Additionally, the product (P2) was mixed with each of polymerizable unsaturated compounds (A2) to (A8), described later, to obtain mixed solutions in the same manner as described above. Then, the compatibility of each mixed solution was evaluated according to the same criteria as above. Table 1 shows the evaluation results.
Determination of Compatibility
  A: Homogeneous, transparent; good compatibility
  B: Slightly cloudy or flickers when shaken; poor compatibility
  C: Obviously cloudy, or at least one of separation, aggregation, sedimentation, and gelation was observed; bad compatibility
Polymerizable Unsaturated Compound
  A1: HDDA (trade name, manufactured by Daicel-Cytec Company, Ltd.; 1,6-hexanediol diacrylate)
  A2: Aronix M-140 (trade name, manufactured by Toagosei Co., Ltd.; N-acryloyloxyethyl hexahydrophthalimide)
  A3: Aronix M-325 (trade name, manufactured by Toagosei Co., Ltd.; ε-caprolactone-modified tris(acryloxyethyl)isocyanurate)
  A4: Trimethylolpropane diacrylate
  A5: Pentaerythritol diacrylate
  A6: Pentaerythritol triacrylate
  A7: Aronix M-403 (trade name, manufactured by Toagosei Co., Ltd.; dipentaerythritol penta- and hexa-acrylate)
  A8: Aronix M-1200 (trade name, manufactured by Toagosei Co., Ltd.; bifunctional urethane acrylate oligomer)

Examples 7 to 10 and Comparative Example 2

The compatibility of each of the products (P4, P5, P6, P8, and P9) obtained in Examples 2 to 5 and Comparative Example 1, respectively, with each of the polymerizable unsaturated compounds was evaluated in a solution state, in the same manner as in Example 6. Table 1 shows the evaluation results.

TABLE 1

| | | Polymerizable unsaturated compound | | | | | | | |
|---|---|---|---|---|---|---|---|---|---|
| | | A1 | A2 | A3 | A4 | A5 | A6 | A7 | A8 |
| Ex. 6 | Product (P2) | A | A | A | A | A | A | A | A |
| Ex. 7 | Product (P4) | A | A | A | A | A | A | A | A |
| Ex. 8 | Product (P5) | A | A | A | A | A | A | A | A |
| Ex. 9 | Product (P6) | A | A | A | A | A | A | A | A |
| Ex. 10 | Product (P8) | A | A | A | A | A | A | A | A |
| Comp. Ex. 2 | Product (P9) | A | B | C | B | B | B | B | C |

Example 11

Using active energy ray-curable compositions comprising the silsesquioxane compounds of the present invention, the compatibility of each product with each of the polymerizable unsaturated compounds was evaluated. The test procedure is described below.

The product (P2) solution having a nonvolatile content of 50% (100 parts) obtained in Example 1, 50 parts of the polymerizable unsaturated compound (A1), 3.0 parts of 1-hydroxy-cyclohexyl-phenyl-ketone (photoinitiator), and 0.5 parts of 2,4,6-trimethylbenzoyl-diphenyl-phosphine oxide (photoinitiator) were mixed. The mixture was diluted with ethyl acetate to a nonvolatile content of 30%, followed by stirring, thereby preparing an active energy ray-curable composition.

Then, the active energy ray-curable composition was applied on an intermediate plate (Note 1) to a film thickness of 10 μm (when dried) using an applicator, and dried at 80° C. for 10 minutes to remove the solvent. Subsequently, using a high-pressure mercury vapor lamp (80 W/cm), the coating film was cured by irradiation with UV light (peak top wavelength: 365 nm) at a radiation dose of 2,000 mJ/cm². The appearance of the cured coating film was visually observed, and the dissolved state was evaluated according to the following criteria. Table 4 shows the evaluation results.

Additionally, using the same formulation as above except that each of the polymerizable unsaturated compounds (A2) to (A8) was used in place of the polymerizable unsaturated compound (A1), active energy ray-curable compositions each comprising one of the polymerizable unsaturated compounds (A2) to (A8) were prepared. Then, coating films cured under the same conditions as above were prepared. The coating films were visually observed, and the dissolved state was evaluated according to the following criteria. Table 2 shows the evaluation results.

(Note 1) Intermediate plate: ELECRON GT-10 (trade name, manufactured by Kansai Paint Co., Ltd.; a cationic electrodeposition coating composition) was applied by electrodeposition to a cold rolled steel plate (0.8×150×70 mm) treated using Palbond #3020 (trade name, manufactured by Nihon Parkerizing Co., Ltd.; a zinc phosphate treating agent) to a film thickness of 20 μm, and baked and dried at 170° C. for 30 minutes to form an electrodeposition coating film. The electrodeposition coating film was spray-coated with WP-300 (trade name, manufactured by Kansai Paint Co., Ltd.; an aqueous intermediate coating composition) to a cured film thickness of 25 μm, and baked and dried in an electric hot air dryer at 140° C. for 30 minutes to prepare an intermediate plate.
Determination of Compatibility
  A: Homogeneous, transparent; good compatibility
  B: Slightly cloudy; poor compatibility
  C: Obviously cloudy, or at least one of aggregation, seeding, and crawling was observed; bad compatibility Examples 12 to 15 and Comparative Example 3

Active energy ray-curable compositions were prepared in the same manner as in Example 11 except that each of the product solutions (P4, P5, P6, P8, and P9) obtained in Examples 2 to 5 and Comparative Example 1 was used in place of the product (P2) solution having a nonvolatile content of 50%. Subsequently, the active energy ray-curable compositions were cured under the same conditions as in Example 11 to form coating films, and the compatibility of each product with each polymerizable unsaturated compound was evaluated. Table 2 shows the evaluation results.

TABLE 2

| | Polymerizable unsaturated compound | | | | | | | |
|---|---|---|---|---|---|---|---|---|
| | A1 | A2 | A3 | A4 | A5 | A6 | A7 | A8 |
| Ex. 11 Product (P2) | A | A | A | A | A | A | A | A |
| Ex. 12 Product (P4) | A | A | A | A | A | A | A | A |
| Ex. 13 Product (P5) | A | A | A | A | A | A | A | A |
| Ex. 14 Product (P6) | A | A | A | A | A | A | A | A |
| Ex. 15 Product (P8) | A | A | A | A | A | A | A | A |
| Comp. Ex. 3 Product (P9) | A | C | C | C | C | C | C | C |

Examples 16 to 22

Active energy ray-curable compositions were prepared using the formulations shown in Table 3 in the same manner as the method for preparing active energy ray-curable compositions and the method for preparing cured coating films in Example 11. Then, cured coating films with a film thickness of 10 μm (when dried) were formed on intermediate plates (Note 1) to obtain test panels. Each of the obtained test panels was evaluated for scratch resistance and weather resistance. Table 3 shows the evaluation results.

Scratch Resistance

Each of the coating films was rubbed against commercially available steel wool (#0000), and the coating film was visually observed and evaluated according to the following criteria.

A: No scratching, cracking, or peeling, or slight scratching but satisfactory from a practical standpoint B: Scratched C: Cracked, peeled, significantly scratched, etc.

Weather Resistance

Each of the obtained test panels was subjected to a 1000-hour test using a Sunshine Weather-O-Meter. Then, the coating film of the panel was visually observed and evaluated according to the following criteria.

A: No abnormalities, or slightly blistered, discolored, change in gloss, peeled, etc., but satisfactory from a practical standpoint B: Blistered, discolored, change in gloss, peeled, etc.

C: Remarkably blistered, discolored, change in gloss, peeled, etc.

TABLE 3

| | | | Ex. 16 | Ex. 17 | Ex. 18 | Ex. 19 | Ex. 20 | Ex. 21 | Ex. 22 |
|---|---|---|---|---|---|---|---|---|---|
| Active energy ray-curable composition | Product | P1 | 50 | 50 | 50 | | | | |
| | | P2 | | | | 50 | | | |
| | | P4 | | | | | 50 | | |
| | | P6 | | | | | | 50 | |
| | | P7 | | | | | | | 50 |
| | Polymerizable unsaturated compound | A2 | 50 | | | 50 | | | 50 |
| | | A3 | | 50 | | | 50 | | |
| | | A8 | | | 50 | | | 50 | |
| | 1-hydroxy-cyclohexyl-phenyl-ketone | | 3.0 | 3.0 | 3.0 | 3.0 | 3.0 | 3.0 | 3.0 |
| | 2,4,6-trimethylbenzoyl-diphenyl-phosphine oxide | | 0.5 | 0.5 | 0.5 | 0.5 | 0.5 | 0.5 | 0.5 |
| Scratch resistance | | | A | A | A | A | A | A | A |
| Weather resistance | | | A | A | A | A | A | A | A |

The numbers in the formulations denote nonvolatile contents.

The invention claimed is:

1. A silsesquioxane compound comprising organic groups each directly attached to a silicon atom of the compound, wherein at least one of the organic groups is an organic group having one or more urethane bonds and one (meth)acryloyloxy group, and the organic group having one or more urethane bonds and one (meth)acryloyloxy group is an organic group represented by the following formula (A):

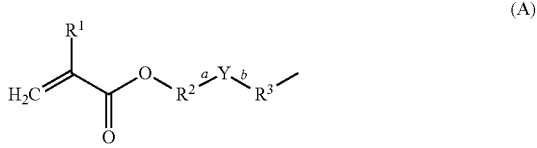

(A)

wherein $R^1$ represents a hydrogen atom or a methyl group, $R^2$ represents a $C_{1-10}$ divalent hydrocarbon group, $R^3$ represents a $C_{1-10}$ divalent hydrocarbon group, and Y represents

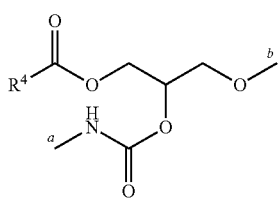

wherein R⁴ represents a substituted or unsubstituted $C_{1-6}$ monovalent hydrocarbon group; or

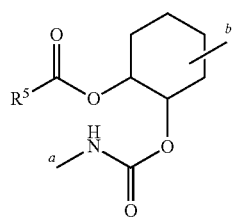

wherein R⁵ represents a substituted or unsubstituted $C_{1-6}$ monovalent hydrocarbon group.

2. The silsesquioxane compound according to claim 1, wherein the weight average molecular weight is 1,000 to 100,000.

3. An active energy ray-curable composition comprising the silsesquioxane compound according to claim 1, and a photoinitiator.

4. The active energy ray-curable composition according to claim 3, further comprising a polymerizable unsaturated compound.

* * * * *